(12) United States Patent
Cianci et al.

(10) Patent No.: US 7,332,125 B2
(45) Date of Patent: **\*Feb. 19, 2008**

(54) SYSTEM AND METHOD FOR PROCESSING BLOOD

(75) Inventors: James P. Cianci, Walpole, MA (US); Thomas D. Headley, Scottsdale, AZ (US); Edward T. Powers, Hampton Falls, NH (US)

(73) Assignee: Haemonetics Corporation, Braintree, MA (US)

( * ) Notice: Subject to any disclaimer, the term of this patent is extended or adjusted under 35 U.S.C. 154(b) by 516 days.

This patent is subject to a terminal disclaimer.

(21) Appl. No.: 10/462,373

(22) Filed: Jun. 16, 2003

(65) Prior Publication Data

US 2004/0147865 A1 Jul. 29, 2004

Related U.S. Application Data

(63) Continuation-in-part of application No. 09/271,627, filed on Mar. 17, 1999, now abandoned, and a continuation-in-part of application No. 09/733,624, filed on Dec. 8, 2000, now Pat. No. 6,824,506, and a continuation-in-part of application No. 09/271,594, filed on Mar. 17, 1999, now Pat. No. 6,632,191, which is a continuation-in-part of application No. 08/843,218, filed on Apr. 14, 1997, now Pat. No. 6,099,491, which is a continuation of application No. 08/322,601, filed on Oct. 13, 1994, now Pat. No. 5,733,253, which is a continuation-in-part of application No. 08/835,680, filed on Apr. 9, 1997, now Pat. No. 6,007,509, which is a continuation of application No. 08/482,617, filed on Jun. 7, 1995, now Pat. No. 5,651,766.

(51) Int. Cl.
*A61M 1/00* (2006.01)
*A61M 37/00* (2006.01)

(52) U.S. Cl. ................. 422/44; 604/4.01; 604/6.09

(58) Field of Classification Search ............... 604/4.01, 604/6.1, 6.01–6.09, 6.11, 6.15, 6.16; 422/44; 210/781–782, 767, 784, 739, 741; 494/11, 494/36–38, 10, 28, 40–45, 56, 57, 60–64
See application file for complete search history.

(56) References Cited

U.S. PATENT DOCUMENTS 2,661,150 A 12/1953 Abbott, Jr. ................. 233/27
(Continued)

FOREIGN PATENT DOCUMENTS

EP 0349188 * 1/1990
(Continued)

*Primary Examiner*—Patricia Bianco

(57) ABSTRACT

A system for filtering and processing blood that is simple to implement and that reduces the need for human intervention. The system may be used to collect red blood cells (RBCs). For such a system, a disposable set may be provided with an inlet port, an RBC container, a centrifuge rotor having a variable total volume, and a filter, along with tubing connecting the port, the container, the rotor and the filter. The filter is located in tubing between the inlet port and the rotor. A control unit is also provided and includes a spinner in which the rotor may be held, a flow-control arrangement for controlling flow among the various components of the disposable set, and an electronic controller. The whole blood is directed by the flow-control arrangement from the inlet through the filter to the rotor. The rotor includes an elastic diaphragm, and the control unit's flow-control arrangement includes a pump or other device for applying a positive and negative pressure to the rotor's elastic diaphragm. The spinner rotates the rotor so as to separate the whole blood into plasma and RBCs. Preferably, the plasma is urged out of the rotor first and returned to the donor, while the rotor is still being spun. After the plasma has been removed from the rotor, the RBCs are urged from the rotor to an RBC container. In preferred embodiments, the filter is a white blood cell filter, so that white blood cells are filtered from the blood before it reaches the rotor.

10 Claims, 3 Drawing Sheets

U.S. PATENT DOCUMENTS

| | | | | |
|---|---|---|---|---|
| 3,096,283 | A | 7/1963 | Hein | 233/20 |
| 3,239,136 | A | 3/1966 | Hein | 233/1 |
| 3,244,362 | A | 4/1966 | Hein | 233/27 |
| 3,244,363 | A | 4/1966 | Hein | 233/28 |
| 3,456,875 | A | 7/1969 | Hein | 233/24 |
| 3,565,330 | A | 2/1971 | Latham, Jr. | 233/21 |
| 3,581,981 | A | 6/1971 | Latham, Jr. | 233/21 |
| 3,675,846 | A | 6/1972 | Drucker | 233/26 |
| 3,706,412 | A | 12/1972 | Latham, Jr. | 233/1 B |
| 3,737,096 | A | 6/1973 | Jones et al. | 233/19 |
| 3,768,653 | A | 10/1973 | Brumfield | 210/188 |
| 3,866,608 | A | 2/1975 | Reynolds et al. | 128/276 |
| 3,899,128 | A | 8/1975 | Joyce | 233/32 |
| 4,006,745 | A | 2/1977 | Sorenson et al. | 128/214 R |
| 4,007,871 | A | 2/1977 | Jones et al. | 233/27 |
| 4,010,894 | A | 3/1977 | Kellogg et al. | 233/27 |
| 4,033,345 | A | 7/1977 | Sorenson et al. | 128/214 R |
| 4,047,526 | A | 9/1977 | Reynolds et al. | 128/214 R |
| 4,054,523 | A | 10/1977 | Ingenito et al. | 210/188 |
| 4,056,224 | A | 11/1977 | Lolachi | 233/14 |
| 4,082,217 | A | 4/1978 | Westberg | 233/25 |
| 4,086,924 | A | 5/1978 | Latham, Jr. | 128/214 |
| 4,115,277 | A | 9/1978 | Swank | 210/436 |
| 4,142,670 | A | 3/1979 | Ishimaru et al. | 233/20 |
| 4,151,844 | A | 5/1979 | Cullis et al. | 128/214 |
| 4,285,464 | A | 8/1981 | Latham, Jr. | 233/26 |
| 4,300,717 | A | 11/1981 | Latham, Jr. | 233/1 |
| 4,303,193 | A | 12/1981 | Latham, Jr. | 233/23 |
| 4,321,921 | A | 3/1982 | Laszczower | 120/276 |
| 4,387,848 | A | 6/1983 | Kellogg et al. | 494/81 |
| 4,424,053 | A | 1/1984 | Kurtz et al. | 604/4 |
| 4,430,072 | A | 2/1984 | Kellogg et al. | 494/45 |
| 4,447,221 | A | 5/1984 | Mulzet | 494/45 |
| 4,457,747 | A | 7/1984 | Tu | 604/4 |
| 4,479,760 | A | 10/1984 | Bilstad et al. | 417/395 |
| 4,482,342 | A | 11/1984 | Lueptow et al. | 494/21 |
| 4,530,691 | A | 7/1985 | Brown | 494/45 |
| 4,561,868 | A | 12/1985 | von Reis et al. | 55/319 |
| 4,643,714 | A | 2/1987 | Brose | 604/4 |
| 4,647,279 | A | 3/1987 | Mulzet et al. | 494/45 |
| 4,673,423 | A | 6/1987 | Yumlu | 55/319 |
| 4,680,025 | A | 7/1987 | Kruger et al. | 604/6 |
| 4,704,203 | A | 11/1987 | Reed | 210/188 |
| 4,708,712 | A | 11/1987 | Mulzet | 494/45 |
| 4,734,089 | A | 3/1988 | Cullis | 494/27 |
| 4,743,371 | A | 5/1988 | Servas et al. | 210/188 |
| 4,758,337 | A | 7/1988 | Köhn et al. | 210/94 |
| 4,806,252 | A | 2/1989 | Brown et al. | 210/744 |
| 4,850,995 | A | 7/1989 | Tie et al. | 604/6 |
| 4,889,524 | A | 12/1989 | Fell et al. | 494/12 |
| 4,898,572 | A | 2/1990 | Surugue new Lesnier et al. | 604/4 |
| 4,911,833 | A | 3/1990 | Schoendorfer et al. | 210/167 |
| 4,934,995 | A | 6/1990 | Cullis | 494/45 |
| 4,940,543 | A | 7/1990 | Brown et al. | 210/369 |
| 4,954,251 | A | 9/1990 | Barnes et al. | 210/806 |
| 4,968,295 | A | 11/1990 | Neumann | 604/6 |
| 4,983,158 | A | 1/1991 | Headley | 494/41 |
| 4,985,153 | A | 1/1991 | Kuroda et al. | 210/782 |
| 5,015,388 | A | 5/1991 | Pusineri et al. | 210/641 |
| 5,039,401 | A | 8/1991 | Columbus et al. | 210/117 |
| 5,045,048 | A | 9/1991 | Kaleskas et al. | 494/41 |
| 5,055,198 | A | 10/1991 | Shettigar | 210/650 |
| 5,112,298 | A | 5/1992 | Prince et al. | 604/6 |
| 5,114,396 | A | 5/1992 | Unger et al. | 494/37 |
| 5,133,703 | A | 7/1992 | Boehringer et al. | 604/317 |
| 5,141,486 | A | 8/1992 | Antwiler | 494/37 |
| 5,154,716 | A | 10/1992 | Bauman et al. | 604/410 |
| 5,174,894 | A | 12/1992 | Ohsawa et al. | 210/86 |
| 5,183,569 | A | 2/1993 | Kyriacou | 210/636 |
| 5,215,519 | A | 6/1993 | Shettigar | 604/4 |
| 5,217,426 | A | 6/1993 | Bacehowski et al. | 494/45 |
| 5,217,427 | A | 6/1993 | Cullis | 494/45 |
| 5,223,154 | A | 6/1993 | MacPherson, Jr. et al. | 210/790 |
| 5,234,403 | A | 8/1993 | Yoda et al. | 604/4 |
| 5,273,517 | A | 12/1993 | Barone et al. | 494/37 |
| 5,277,701 | A | 1/1994 | Christie et al. | 604/4 |
| 5,298,016 | A | 3/1994 | Gordon | 609/4 |
| 5,300,060 | A | 4/1994 | Nelson | 604/410 |
| 5,316,540 | A | 5/1994 | McMannis et al. | 494/37 |
| 5,318,512 | A | 6/1994 | Neumann | 604/6 |
| 5,368,542 | A | 11/1994 | McMannis et al. | 494/45 |
| 5,386,734 | A | 2/1995 | Pusionelli | 73/863.21 |
| 5,387,174 | A | 2/1995 | Rochat | 494/10 |
| 5,387,187 | A | 2/1995 | Fell et al. | 604/6 |
| 5,411,705 | A | 5/1995 | Thor et al. | 422/45 |
| 5,417,650 | A | 5/1995 | Gordon | 604/4 |
| 5,437,598 | A | 8/1995 | Antwiler | 494/1 |
| 5,470,483 | A | 11/1995 | Bene et al. | 210/741 |
| 5,484,396 | A | 1/1996 | Nificy | 604/4 |
| 5,543,062 | A | 8/1996 | Nishimura | 210/782 |
| 5,651,766 | A * | 7/1997 | Kingsley et al. | 604/6.04 |
| 5,674,173 | A | 10/1997 | Hlavinka et al. | 494/17 |
| 5,728,060 | A | 3/1998 | Kingsley et al. | 604/4 |
| 5,733,253 | A | 3/1998 | Headley et al. | 604/4 |
| 5,770,073 | A | 6/1998 | Bach et al. | 210/472 |
| 5,779,660 | A | 7/1998 | Kingsley et al. | 604/6 |
| 5,800,721 | A | 9/1998 | McBride | 210/506 |
| 5,879,624 | A | 3/1999 | Boehringer et al. | 422/44 |
| 5,885,239 | A | 3/1999 | Headley et al. | 604/4 |
| 6,099,491 | A | 8/2000 | Headley et al. | 604/4 |
| 6,106,727 | A | 8/2000 | Krasnoff et al. | 210/739 |
| 6,632,191 | B1 * | 10/2003 | Headley et al. | 604/6.01 |

FOREIGN PATENT DOCUMENTS

| | | |
|---|---|---|
| EP | 0 578 086 A1 | 1/1994 |
| EP | 0 771 570 A1 | 5/1997 |
| EP | 0 852 141 A1 | 7/1998 |
| FR | 2 258 898 | 1/1975 |
| GB | 2 047 110 A | 11/1980 |
| WO | WO 85/02566 | 6/1985 |
| WO | WO 92/16304 | 10/1992 |
| WO | WO 96/11747 | 4/1996 |

* cited by examiner

SYSTEM AND METHOD FOR PROCESSING BLOOD

RELATED APPLICATIONS

The present application is a continuation-in-part of U.S. patent application Ser. No. 09/271,627, filed Mar. 17, 1999, now abandoned entitled "System and Method for Processing Blood" for an invention of Cianci.

The present application is also a continuation-in-part of U.S. patent application Ser. No. 09/733,624, filed Dec. 8, 2000, now U.S. Pat. No. 6,824,506 entitled "Shaped Diaphragm for a Centrifuge System Rotor" for an invention of Lamphere and Headley.

The present application is also a continuation-in-part of U.S. patent application Ser. No. 09/271,594, filed Mar. 17, 1999, now U.S. Pat. No. 6,632,191 entitled "System and Method for Separating Blood Components"; which in turn is a continuation-in-part of U.S. patent application Ser. No. 08/843,218, filed Apr. 14, 1997, now issued as U.S. Pat. No. 6,099,491, entitled "Fluid Separation System; which in turn is a continuation of U.S. patent application Ser. No. 08/322,601, filed Oct. 13, 1994, entitled "Fluid Separation System" for an invention of Headley and Powers, now issued as U.S. Pat. No. 5,733,253.

U.S. patent application Ser. No. 09/271,594 is also a continuation-in-part of U.S. patent application Ser. No. 08/835,680, filed Apr. 9, 1997, now issued as U.S. Pat. No. 6,007,509, entitled "Blood Collection and Separation System"; which in turn is a continuation of U.S. patent application Ser. No. 08/482,617, filed Jun. 7, 1995 for an invention of Kingsley, Headley and Halpern, now issued as U.S. Pat. No. 5,651,766.

All these applications are incorporated herein by reference.

TECHNICAL FIELD

This invention generally relates to systems and methods for processing blood and other biological fluids.

BACKGROUND

Centrifugal biological-fluid-processing systems have been in existence for some time. Some are used to collect high concentrations of certain components of a person's blood while others are used to further process blood components by washing, concentrating or otherwise purifying the blood component of interest. Some of these systems are used to process biological fluids other than blood. Filtration systems are also used for processing blood and other biological fluids.

The centrifugal systems (hereinafter called blood-processing systems) generally fall into two categories, continuous-flow devices and discontinuous-flow devices.

In continuous-flow systems, whole blood from the donor or patient flows through one conduit into the spinning rotor where the components are separated. The component of interest is collected and the unwanted components are returned to the donor through a second conduit on a continuous basis as more whole blood is being drawn. Because the rate of drawing and the rate of return are substantially the same, the extracorporeal volume, or the amount of blood that is out of the donor or patient at any given time in the procedure, is relatively small. These systems typically employ a belt-type rotor, which has a relatively large diameter but a relatively small (typically 100 ml or less) processing volume. Although continuous-flow systems have the advantage that the amount of blood that must be outside the donor or patient can be relatively small, they have the disadvantage that the diameter of the rotor is large. These systems are, as a consequence, large; furthermore, they are complicated to set up and use. These devices are used almost exclusively for the collection of platelets.

In discontinuous-flow systems, whole blood from the donor or patient also flows through a conduit into the rotor where component separation takes place. These systems employ a bowl-type rotor with a relatively large (typically 200 ml or more) volume that must be filled with blood before any of the desired components can be harvested. When the bowl is full, the drawing of fresh blood is stopped, and the unwanted components are returned to the donor or patient through the same conduit intermittently, in batches, rather than on a continuous basis. When the return has been completed, whole blood is again drawn from the donor or patient, and a second cycle begins. This process continues until the desired amount of component has been collected.

Discontinuous-flow systems have the advantage that the rotors are relatively small in diameter but have the disadvantage that the extracorporeal volume is large. This, in turn, makes it difficult or impossible to use discontinuous systems on people whose size and weight will not permit the drawing of the amount of blood required to fill the rotor. Discontinuous-flow devices are used for the collection of platelets and/or plasma, and for the concentration and washing of red blood cells (RBCs). They are used to reconstitute previously frozen RBCs and to salvage RBCs lost intraoperatively. Because the bowls in these systems are rigid and have a fixed volume, however, it is difficult to control the hematocrit of the final product, particularly if the amount of blood salvaged is insufficient to fill the bowl with RBCs.

One RBC-washing system marketed by Cobe Laboratories is made almost entirely of flexible PVC. It has the advantage of being able to vary the volume of the rotor to control the final hematocrit but has the disadvantage of being limited to a rather flat, wide pancake-like shape due to manufacturing constrictions. The Cobe system controls the rotor volume by pumping a hydraulic fluid—a liquid—in or out of a bladder that rotates with and squeezes the blood out of rotor. The Cobe system takes up a fairly large amount of space, and its flexible pancake-shaped rotor is awkward to handle. The Cobe system does not permit blood to flow into and out of its rotor at the same time. The Cobe system also does not permit blood to be pulled into the rotor by suction. The Cobe rotor is usually filled with blood by gravity, although the blood may be pumped into the rotor. After the blood has been separated, it is squeezed out of the rotor by pumping hydraulic fluid into the bladder.

Haemonetics Corp. and others have provided systems to collect blood shed during surgery, concentrate and wash the RBCs, and return them to the patient. Existing systems typically use a 3 liter reservoir to collect and coarse filter the blood vacuumed from the surgical site and a separate processing set including a special centrifugal processing chamber to wash and concentrate the red blood cells in order that they may be safely reinfused to the patient. Because of their cost and complexity of use, these systems are used only in operations where relatively large blood loss is expected. The prior-art rotors used for processing blood collected during an operation, made by Haemonetics Corp. and others, must be completely filled with RBCs before any processing can occur, and thus the process takes more time and is not appropriate for use with small people or for an operation with low blood loss. Because the volume of the processing chamber is fixed, the final concentration of the RBCs in the last cycle of the process cannot be easily controlled.

Solco Basel AG makes a filter-based system for wound drains. This wound-drain system has the disadvantage that the blood returned to the patient contains, in addition to the RBCs, substances that may be deleterious to the patient.

There exists the need, therefore, for a centrifugal system for processing blood and other biological fluids, that is compact and easy to use and that does not have the disadvantages of prior-art discontinuous-flow systems. There is also a need for improving the way that blood is processed in a variety of applications, such as apheresis, intraoperative blood-salvage systems, and wound drains, so that the blood processing takes less time, requires less cumbersome equipment, and/or reduces harmful side effects in the patient or donor.

SUMMARY OF THE INVENTION

The present invention is directed to systems and methods for collecting, filtering, and separating blood components, and in particular, systems and methods that are simple to use and that reduce the need for human intervention. A disposable set is provided with (i) a port (e.g., a cannula inserted into a vein of the donor) for permitting whole blood to flow from a whole blood source into the disposable set, (ii) a filter, which may be for example, a white blood cell (WBC) filter (iii) a separation container wherein the whole blood is separated into components (for example, a centrifuge rotor or other separation means), (iv) a blood-component container for storing a separated blood component, and (v) tubing connecting the port, the filter, the separation container and the blood-component container. The port acts as an inlet allowing whole blood to flow into the disposable set. The filter is located between the port (i.e., the inlet) and the separation. The inlet port is connected to the donor, and whole blood is drawn from the donor through the port. The whole blood is directed from the port through the filter to the separation container, so that whole blood is filtered before entering the separation container. After the whole blood is separated into a first component and a second component, one of the first and second components is directed from the separation container to the blood-component container.

A preferred embodiment of the present invention is directed to systems and methods for collecting red blood cells from a donor while returning plasma to the donor. The filter is capable of filtering white blood cells from the whole blood. Whole blood is removed from a donor, WBCs are filtered from the whole blood, and the filtered blood is directed to a centrifuge rotor, where the blood is separated into red blood cells (RBCs) and plasma. The plasma may be returned to the donor during the same procedure in which whole blood is drawn from the donor. At one or more times during the collection process, when all the rotor has been emptied of plasma, the red blood cells are urged from the rotor and collected in one or more RBC containers.

In a preferred embodiment, the system for collecting red blood cells includes a disposable set as set forth above, and having a centrifuge rotor for the separation container and an RBC container for the blood-component container. In preferred embodiments, the port also acts as an outlet, so as to permit the return of a separated blood component to the donor; alternatively, a separate outlet port may be provided. The WBC filter is located between the port and the centrifuge rotor. The RBC container is connected to a branch of the tubing leading from the rotor.

Preferably, the centrifuge rotor has a variable total volume. The rotor preferably includes a fixed portion, a rotatable portion and a rotary seal providing a seal between the fixed and rotatable portions, wherein the tubing is connected to the rotor's fixed portion. In order to create a variable total volume, the centrifuge rotor may include in its rotatable portion an elastic diaphragm, which stretches to increase the total volume of the rotor. In such an embodiment, an internal wall is preferably included, for separating the diaphragm from the rotor's fixed portion.

The system also includes a control unit having a spinner in which the rotor may be held. The control unit may include means for varying the volume of the centrifuge rotor by changing the pressure of a gas adjacent the elastic diaphragm. Preferably, a vacuum may be applied to the elastic diaphragm by the control unit, so as to draw blood into the rotor.

In a preferred method of carrying out the invention, the rotor is placed in the spinner, and the port is connected to the donor. After the rotor is placed in the spinner, whole blood may be drawn from the donor through the port. The whole blood is directed from the port through the WBC filter to the rotor, so that white blood cells are filtered from the whole blood. While the donor is still connected to the port, the spinner rotates the rotor so as to separate the whole blood into plasma and red blood cells. The plasma is urged out of the rotor first, while the rotor is still spinning, to be directed back to the donor. The second component is directed from the rotor to the RBC container.

In one embodiment, an inlet port may be used for drawing whole blood, and a separate outlet port may be used for returning the plasma component. In a preferred embodiment, a port is used to draw whole blood and to return the plasma component; in this embodiment, a temporary storage container is used to hold the plasma while whole blood is being collected, and the plasma is returned when the red blood cells are being processed by and urged from the rotor.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Figure 1:
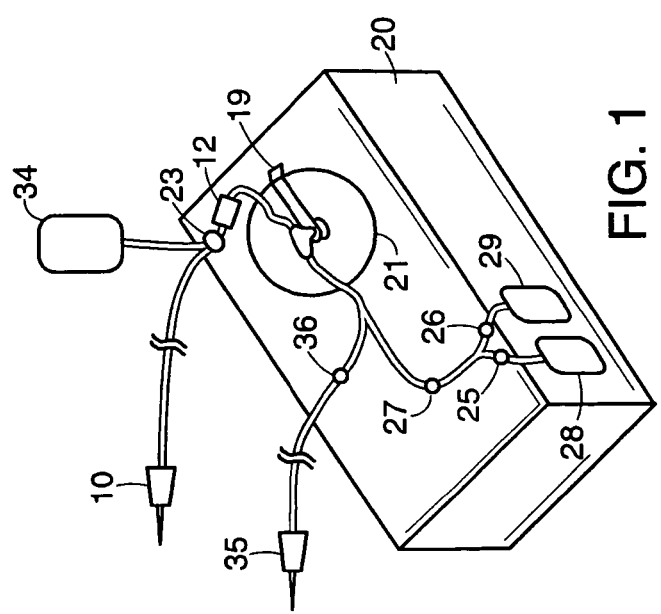
FIG. 1 shows a system according to the present invention.

FIG. 1 shows an embodiment of a system according to the present invention. The system includes a disposable set (such as the one shown in FIG. 3) and a control unit that controls the disposable set. The disposable set includes an inlet port 10, e.g., a cannula, which may act as a connector for attachment to a shunt or other arrangement for permitting whole blood to enter the disposable set from the donor. Tubing connects the various components of the disposable set. The whole blood passes through some of the tubing and flows into the centrifuge rotor 21 mounted in a control unit 20. A filter 12 is located in the tubing between the inlet port 10 and the rotor 21. In preferred embodiments, this filter 12 is a white blood cell (WBC) filter that filters white blood cells from the whole blood; however other types of filters may be utilized, such as a course filter used when collecting blood shed during surgery (for example, as shown in U.S. Pat. No. 6,251,291, entitled "Reservoir-and-Filter System and Method of Use") Performing WBC filtering of the whole blood before separation is easier than filtering the red blood cells after separation, because of the lower density of the whole blood. Filtering the whole blood before separation results in the white blood cells being removed from the plasma as well as the red blood cells.

The filtered blood is spun in the rotor at a sufficiently high speed so as to cause the blood to separate into plasma and red blood cells. The plasma is returned to the donor through an outlet port 35 (e.g., a cannula), while blood is being drawn from the donor. The red blood cells are collected in one or more RBC containers 28, 29.

An anticoagulant bag 34 is preferably connected to the tubing between the inlet port 10 and the filter 12, so as to provide anticoagulant to the whole blood being drawn. A metering valve 23 on and controlled by the control unit may be used to meter the anticoagulant from the anticoagulant container 34 into the whole blood being drawn from the inlet port 10. In lieu of or in addition to valve 23, a peristaltic pump or other flow-inducing arrangement may be used to add the anticoagulant to the whole blood and/or help draw blood from the donor. In a preferred embodiment, the tubing may be modified so that the anticoagulant is added to the whole blood coming from the donor at a point in the tubing much closer to the inlet port 10. (In addition to—or in lieu of—the anticoagulant, a replacement fluid, such as saline, may be added to the whole blood being drawn. After the whole blood has been centrifuged, plasma is returned to the donor along with the replacement fluid. The replacement fluid provides the donor with a volume of fluid to replace the volume of red blood cells that are collected. Adding replacement fluid to the whole blood has an anticoagulating effect. Anticoagulant may be added to the replacement fluid to provide more anticoagulation.)

The rotor 21 preferably has a variable total volume and two ports to permit the introduction of blood into the rotor at the same time a blood component is being removed. In a preferred embodiment, the rotor is of the type shown in FIGS. 10-15 or FIGS. 23-27 in above-referenced U.S. Pat. No. 5,733,253.

Figure 2:
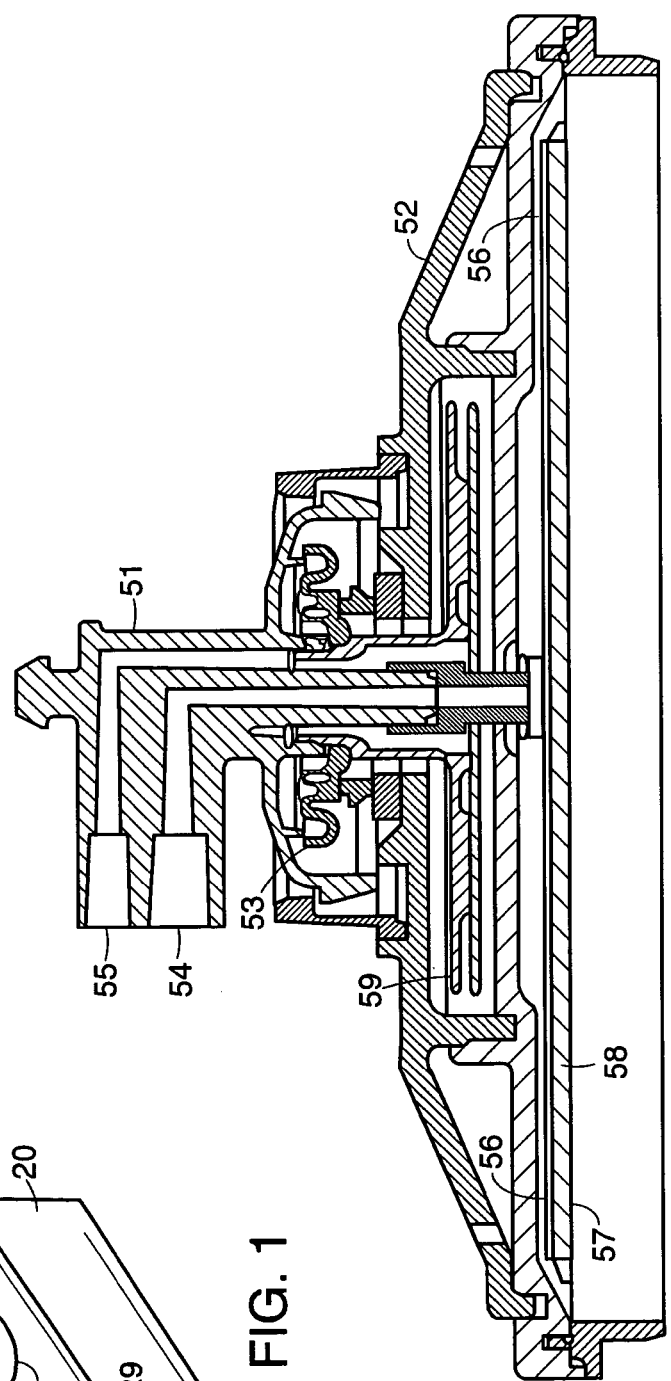
FIG. 2 shows a sectional view of a rotor that may be used in the system of the present invention.

FIG. 2 is a sectional view of a rotor which may be used in the system shown in FIG. 1, and which is a variation on the rotor shown in FIGS. 10-15 of U.S. Pat. No. 5,733,253. The rotor includes a fixed portion 51, which does not rotate and which (as shown in FIG. 1) is held in place by a brace 19 on the control unit 20; a rotatable portion 52, which is held and spun by a chuck in the control unit; and a rotary seal 53, which maintains a seal between the fixed portion and the rotatable portion. The rotary seal preferably works in the same manner as the rotary seal shown in FIGS. 38 and 39 of U.S. Pat. No. 5,733,253: The sealing force applied by the rotary seal 53 is not substantially affected by changes in air pressure within the rotor. The rotary seal is mounted on a base, which may be part of the rotor's fixed portion 51. The rotary seal 53 includes first and second rigid seal members, which surround the axis of rotation, and which spin in relation to each other. As set forth in U.S. Pat. No. 5,733,253, the first rigid seal member and the base define an annular passage between them, and the first rigid seal member has a step portion which extends radially across the annular passage. A spring member surrounds the rotary seal's axis of rotation and is connected to the base and to the first rigid seal member, so that the spring member applies a force pressing the first rigid seal member against the second rigid seal member. A flexible seal member surrounds the axis of rotation and prevents fluid flow between the first rigid seal member and the base. The flexible seal member extends across the annular passage such that pressure from the annular passage exerts forces on the flexible seal member and the step portion which cancel each other, so that the force with which the spring member presses the first rigid seal member against the second rigid seal member is not substantially affected by pressure within the annular passage.

The rotor's fixed portion includes a rotor inlet 54 and a rotor outlet 55, which are connected by tubing with the rest of the disposable set. The tubing of the disposable set has a portion that provides whole blood to the inlet 54 of the rotor 21 and another portion that provides blood components from the rotor's outlet 55 to outlet port 35 and to the RBC-collection containers 28, 29. The rotor inlet 54 leads to a fluid passage down the fixed portion 51 to a pair of channels 56, which are in the rotor's rotatable portion 52. The channels 56 permit the blood that has come from the donor and passed through the WBC filter to flow to the outer perimeter of the rotor's interior volume. Because the rotor's interior volume is defined in part by a flexible, preferably elastic, diaphragm, the rotor has a variable total volume.

Preferably, only two such inflow channels 56 providing fluid communication from the rotor inlet 53 are used, in order to minimize the amount of blood trapped in the rotor when the process is completed, and these two channels are preferably disposed 180" from each other, in order to maintain balance in the rotor. In alternative embodiments, one or more than two inflow channels 56 may be used. The rotor includes an interior wall 58, which together with the flexible diaphragm 57 fully define the rotor's processing chamber. The interior wall 58 includes grooves on its bottom surface (not shown), which permit flow of blood components out of the rotor's processing chamber. In a preferred embodiment, the interior wall 58 includes two of these outflow grooves arranged 180" to each other and at 90" to the inflow channels 56. The outflow grooves lead to holes which pass up through the interior wall 58 to the region adjacent a collector 59. These holes (not shown) provide fluid communication between the outflow grooves and the collector 59, which is part of the rotor's fixed portion 51. The collector 59 collects the blood components flowing out of the processing chamber and directs the blood components up through a vertical passage to the rotor outlet 55.

Blood may be drawn into the rotor 21 by creating a vacuum in the chuck that holds the rotor 21. Alternatively, a peristaltic pump or other flow-inducing arrangement may be used, in lieu of or in addition to valve 23, to draw the whole blood from the port 10 into the rotor 21.

When a sufficient amount of whole blood has entered the rotor 21, the rotor is spun sufficiently fast so as to separate the blood into plasma and red blood cell components. After the blood has separated into plasma and red blood cells, valve 36 is opened, and plasma (and replacement fluid) is urged from the rotor 21 and is directed back to the donor through the outlet port 35. Plasma may be removed from the rotor as filtered blood is continuing to be introduced into the rotor.

Because the plasma component of the blood is being returned to the donor, two units of red blood cells may ordinarily be collected from the donor. In accordance with industry practice, the two units of red blood cells may be stored in two separate containers 28 and 29. In an alternative embodiment, a single container may be used, instead of two containers.

When it is determined that enough red blood cells have been collected, or when the rotor is substantially filled with red blood cells, whatever plasma remains in the rotor is forced from the rotor 21. When substantially all of the plasma has been removed from the rotor, valve 36 is closed and valves 27 and 25 are opened; the red blood cells are urged from the rotor and directed through valves 27 and 25 into the RBC-storage container 28. Since the white blood cells have already been filtered from the whole blood by the WBC filter 12, it is unnecessary in the present system to include a WBC filter between the rotor 21 and the RBC-storage containers 28 and 29.

The RBC-storage containers 28 and 29 are preferably bags and preferably contain RBC preservative (or storage solution). The RBC-storage bags 28 and 29 preferably hold a unit of red blood cells each. When a unit of red blood cells have been delivered to RBC-storage container 28, valve 25 is closed and valve 26 opened, thereby permitting the red blood cells to flow into RBC-storage bag 29. Valves 25, 26, 27 and 36, along with valve 23, are controlled by the control unit 20. This method and system may be modified so that platelets are separately collected in the manner set forth in U.S. Pat. No. 6,296,602, entitled "System and Method for Collecting Platelets and Other Blood Components," listing Thomas D. Headley as an inventor. This patent is incorporated herein by reference.

Depending on the maximum volume of the centrifuge rotor 21 used in relation to the total volume of the two RBC-storage containers 28, 29 used, it may be necessary to go through several cycles of filling the rotor, separating the blood into RBC and plasma components and urging plasma from the rotor until the rotor becomes filled with red blood cells, and at that point, urging the red blood cells from the rotor into one or more of the RBC-storage containers, in order to obtain desired amount (preferably two units) of red blood cells. Once the storage bags 28, 29 are filled with red blood cells, the storage bags are removed from the rest of the disposable set by cutting and heat sealing the tubes leading to the storage bags.

The process described hereinabove is highly automated compared to the prior-art methods of processing blood. A blood-donation technician installs the disposable set into the control unit 20 and inserts the inlet and outlet ports 10, 35 into the donor's arms. The technician, of course, also removes the cannulas from the donor's arms, and cuts and heat seals the tubing leading to the storage bags. The remaining steps of the process may be performed by the control unit: controlling the valves (and any pumps) to direct the flow of blood or blood components; determining when the rotor is sufficiently full; spinning the rotor; urging blood components from the rotor; and determining when the rotor has been emptied of a blood component.

As noted above, in a preferred embodiment of the control unit, each of valves 23, 25, 26, 27 and 36 are controlled by the control unit 20, as is the speed that the rotor 21 is spun. Several of the valves 23, 25, 26, 27 and 36 may be combined into a single valve mechanism. The preferred embodiment of the rotor 21 has a stretchable elastic diaphragm 57 that defines the interior volume of the rotor 21. As discussed in the above-referenced U.S. Pat. Nos. 5,733,253 and 5,651,766, the elastic diaphragm (item 57 of FIG. 2) permits the total volume of the rotor 21 to be varied by varying the air pressure applied to the elastic diaphragm; this air pressure is also preferably controlled by the control unit so as to vary and control the total volume of the rotor 21. This air pressure may also be used to force fluid from the rotor 21 by increasing the air pressure sufficiently or to draw fluid into the rotor 21 by decreasing air pressure sufficiently.

Figure 3:
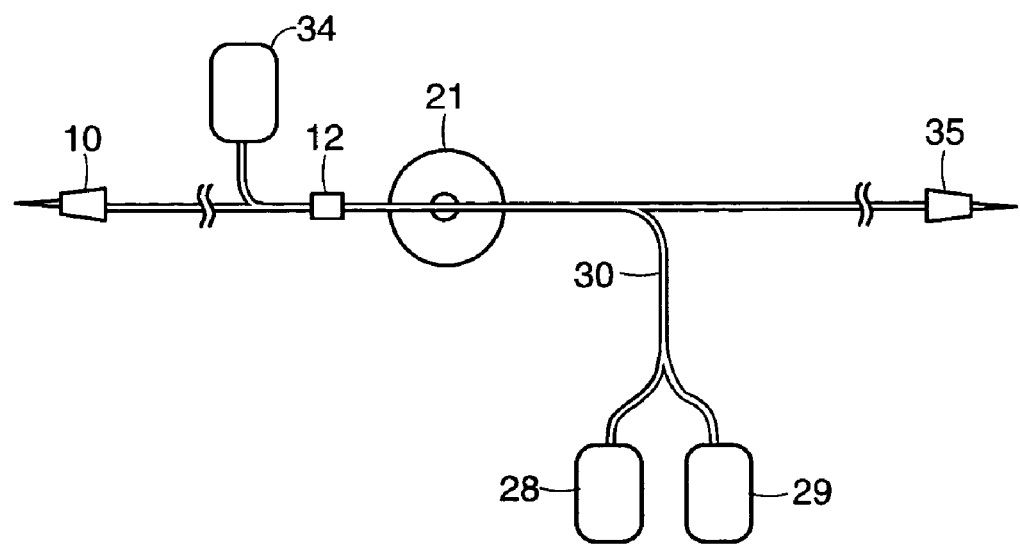
FIG. 3 shows a disposable set that may be used in the system shown in FIG. 1.
Figure 4:
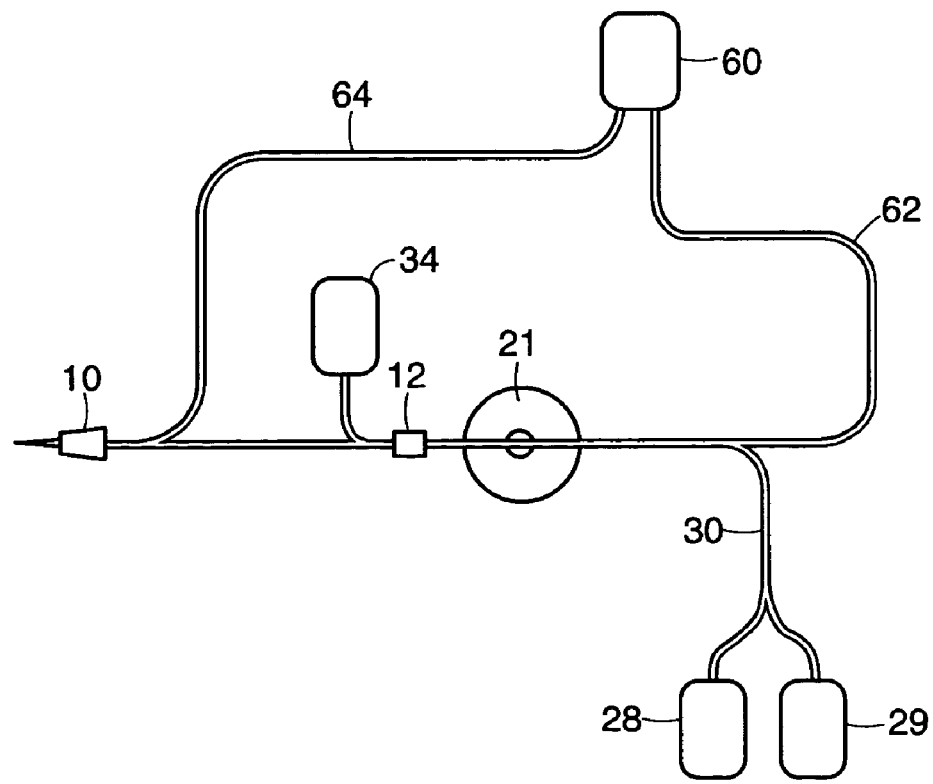
FIG. 4 shows an alternative disposable set.

The disposable set shown in FIGS. 1 and 3, as well as the control unit 20 shown in FIG. 1, may in a preferred embodiment be modified to use a single cannula or port to draw whole blood from the donor and return plasma to the donor. Such a disposable set is shown in FIG. 4. A temporary storage container 60 holds the separated plasma component for return to the donor. The separated plasma component is urged by the control unit from the rotor 21 through a portion 62 of the tubing to the temporary storage container 60. The control unit preferably urges the plasma from the rotor by increasing the gas pressure against the rotor's elastic membrane. Once plasma begins flowing from the rotor, the continued introduction of whole blood to the rotor tends to continue forcing separated plasma out of the rotor. After a desired amount of whole blood has been collected from the donor through port 10 (preferably when the rotor is almost full of red blood cells), the collection of whole blood is suspended, and plasma may be urged from the temporary storage container 60 through another portion 64 of the tubing to the port 10 and the donor. The control unit may be provided with means, such as a peristaltic pump working on tubing portion 64, for effecting and controlling the flow of plasma from the temporary storage container 60 to the port 10. The rest of the disposable set may be same as the disposable set shown in FIG. 3, including a WBC filter 17 in another portion of the tubing leading from the port 10 to the rotor 21, so as to permit the white blood cells to be filtered from the whole blood before it is separated; an anticoagulant container 34 may be attached to this same portion of the tubing. In a preferred embodiment, the anticoagulant container may be connected to a point in the tubing closer to the port 10, so as to introduce the anticoagulant to the whole blood as soon as possible after it is drawn from the donor.

Figure 5:
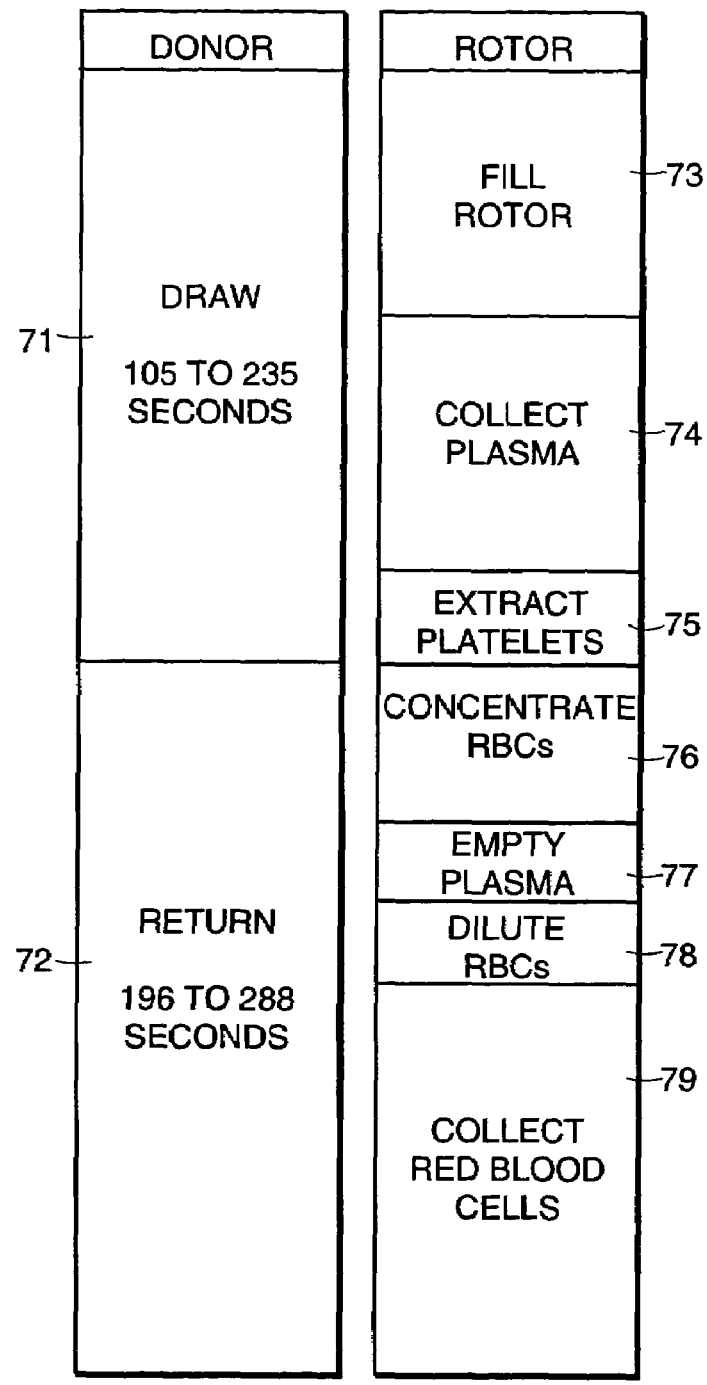
FIG. 5 shows the arrangement of steps in a cycle of a process for collecting red blood cells using the disposable set of FIG. 4.

The process of collecting red blood cells using the disposable set shown in FIG. 4 may involve several cycles of collecting whole blood from the donor and returning the separated plasma component to the donor. FIG. 5 shows an outline of steps in one such cycle. Each cycle is divided up into two periods: a first period 71 in which whole blood is drawn from the donor, i.e., a draw period (which in one embodiment lasts between 105 and 235 seconds), and a second period 72 in which plasma is returned to the donor, i.e., a return period (which lasts between 196 and 288 seconds). During the draw period 71, the rotor—item 21 in FIG. 4—is filled with whole blood from the donor (step 73), and the rotor is spun to separate the blood into plasma and RBC components. Plasma is urged from the rotor to the temporary container 60 (step 74—of course, some of these steps may overlap). In an optional step (step 75), the platelets may be separately collected in the manner set forth in U.S. Pat. No. 6,296,602. (As set forth previously, this patent is incorporated herein by reference.) During the return period 72, the red blood cells are concentrated, by increasing the rotational speed of the centrifuging rotor (step 76), and the remaining plasma is removed from the rotor 21 to the temporary container 60 (step 77). An RBC-storage solution may be added to the red blood cells, diluting the red blood cells (step 78). In the final step of the cycle (step 79), the red blood cells are directed through the portion 30 of the tubing to one of the two storage containers 28 or 29.

When the red blood cells have been moved from the rotor to the storage containers, and when the plasma in the temporary container has been returned to the donor, the cycle may start again with the draw period 71 and the rotor filling step 73. In one embodiment, the total cycle time lasts from 5 to 8.7 minutes (assuming a hematocrit range of 40 to 55 and a draw speed range of 60 to 100 ml/min). Four cycles may be executed, for a total procedure time of 20 to 34.8 minutes.

The disposable sets shown in FIGS. 3 and 4—the storage bags 28, 29, filter 12, centrifuge rotor 21 and the tubing—may be configured in several ways. The tubing may consist solely of tubes which may be squeezed by the control unit to direct flow or to pump in a peristaltic manner. Alternatively, the tubing may contain special valving or pumping components (such as a pumping/valving cassette) which may be acted on by the control unit. The phrase "flow-control arrangement" refers herein to any structure or system for controlling or causing flow of fluid between the various components of the systems of the present invention. Such tubing of the disposable set may be considered an example of return means for permitting return of plasma to the donor.

The control unit shown in FIG. 1 and the disposable set shown in FIGS. 1 and 3 may also be modified, by substituting a plasma collection container for the outlet port 35, to permit the collection of plasma that is free of white blood cells, as well as the collection of red blood cells that are free of white blood cells.

Although the invention has been described with reference to several preferred embodiments, it will be understood by one of ordinary skill in the art that various modifications can be made without departing from the spirit and the scope of the invention, as set forth in the claims herein below.

What is claimed is:

1. A system for processing blood, the system comprising:
    a disposable set having
        a port for permitting the introduction of blood from a whole blood source into the disposable set,
        a variable-volume centrifuge rotor wherein the whole blood is separated into components,
        a filter that is located in a fluid path between the port and rotor, and
        a blood-component container for storing a separated blood component, the blood-component container being in fluid communication with the rotor; and
    a control unit having a flow-control arrangement which urges a blood component from the rotor to the blood-component container after the blood has been separated, the control unit further including means for spinning the rotor and for varying the volume of the rotor.

2. The system according to claim 1, wherein the centrifuge rotor includes an elastic diaphragm which defines the volume of the rotor, and wherein the control unit includes means for varying gas pressure adjacent the elastic diaphragm.

3. The system according to claim 2, wherein the means for varying gas pressure includes means for applying a vacuum to the elastic diaphragm, so as to draw blood into the rotor.

4. The system according to claim 1, wherein the filter is capable of filtering white blood cells from whole blood passing through the filter.

5. A system for collecting red blood cells from a donor, the system comprising:
    a disposable set having
        a port for permitting the introduction of blood from the donor into the disposable set;
        a centrifuge rotor having a variable total volume;
        a filter that is located in a fluid path between the port and rotor;
        return means for permitting return of plasma to the donor, the return means being in fluid communication with the centrifuge rotor; and
        an RBC container in fluid communication with the centrifuge rotor; and
    a control unit having
        a spinner that holds the rotor, the spinner being able to spin the rotor so as to separate blood into blood components; and
        a flow-control arrangement which urges a blood component from the rotor while the rotor is being spun.

6. The system according to claim 5, wherein the control unit further includes means for varying the volume of the rotor.

7. The system according to claim 6, wherein the centrifuge rotor includes an elastic diaphragm which defines the volume of the rotor, and wherein the control unit includes means for varying gas pressure adjacent the elastic diaphragm.

8. The system according to claim 7, wherein the means for varying gas pressure includes means for applying a vacuum to the elastic diaphragm, so as to draw blood into the rotor.

9. The system according to claim 7, wherein the filter is capable of filtering white blood cells from whole blood passing through the filter.

10. The system according to claim 5, wherein the return means includes a temporary storage container.

* * * * *